(12) United States Patent
Puzas (10) Patent No.: US 7,386,337 B2
(45) Date of Patent: Jun. 10, 2008

(54) CORRECTION OF DUAL ENERGY X-RAY ABSORPTIOMETRY MEASUREMENTS BASED ON BODY LEAD LEVELS

(75) Inventor: J. Edward Puzas, Pittsford, NY (US)

(73) Assignee: University of Rochester, Rochester, NY (US)

( * ) Notice: Subject to any disclaimer, the term of this patent is extended or adjusted under 35 U.S.C. 154(b) by 976 days.

(21) Appl. No.: 10/428,367

(22) Filed: May 2, 2003

(65) Prior Publication Data

US 2003/0223537 A1 Dec. 4, 2003

Related U.S. Application Data

(60) Provisional application No. 60/378,303, filed on May 6, 2002.

(51) Int. Cl.
*A61B 5/05* (2006.01)

(52) U.S. Cl. ............... 600/407; 378/44; 378/45; 378/50; 378/53; 378/54; 378/92; 600/425

(58) Field of Classification Search .......... 378/44, 378/53, 54, 92
See application file for complete search history.

(56) References Cited

OTHER PUBLICATIONS

Nielsen et al. Influence of strontium on bone mineral density and bone mineral content measurements by dual X-ray absorptiometry. Journal of Clinical Densitometry. 2(4):371-9. 1999.*

Todd, A C. Coherent scattering and matrix correction in bone-lead measurements. Phys. Med. Biol. 45:pp. 1953-1963. 2000.*

Escribano et al. Effect of lead on bone development and bone mass: a morphometric, densitometric and histomorphometric study in growing rats. Calcif Tissue Int. 60:200-203. 1997.*

Gordon, Christopher L., et al., An upgraded [109] CD K X-ray fluorescence bone PB measurement, Human Body Composition, 1993, 285-288, Plenum Press, New York, USA.

Gulson, B. L., et al., Contribution of tissue lead to blood lead in adult female subjects based on stable lead isotope methods, J. Lab. Clin. Med., Jun. 1995, 703-712, vol. 125, No. 6, USA.

Hoppin, Jane A., Validation of K-XRF bone lead measurement in young adults, Environmental Health Perspectives, Jan. 1995, vol. 103, No. 1, article obtained from INTERNET address http://www.ehponline.org/members/1995/103-1/hoppin-full.html.

Gruber, Helen E., Osteopenia induced by long-term, low- and high-level exposure of the adult rat to lead, Mineral and Electrolyte Metabolism, 1997, 65-73, vol. 23, Karger A.G. Basel, Switzerland.

(Continued)

*Primary Examiner*—Brian L. Casler
*Assistant Examiner*—Parikha S. Mehta
(74) *Attorney, Agent, or Firm*—McDermott Will & Emery LLP (57) ABSTRACT

Methods for correcting a bone density value for an effect of lead are disclosed. One method includes determining an apparent bone density in a patient; applying a correction factor to the apparent bone density, the correction factor being based on a blood lead level; and deriving a corrected bone density value for the patient.

19 Claims, 4 Drawing Sheets

Correction for Lead effect on DEXA $BMD_{corr} = BMD_{meas} (mBLL+b)/b$

OTHER PUBLICATIONS

Escribano, A., et al., Effect of lead on bone development and bone mass: a morphometric, densitometric, and histomorphometric study in growing rats, Calcified Tissue international, 1997, pp. 200-203, vol. 60, Springer-Verlag New York Inc.

* cited by examiner

CORRECTION OF DUAL ENERGY X-RAY ABSORPTIOMETRY MEASUREMENTS BASED ON BODY LEAD LEVELS

CROSS-REFERENCE TO RELATED APPLICATIONS

This application claims the benefit of U.S. Provisional Application No. 60/378,303, filed May 6, 2002, the entirety of which is hereby incorporated by reference.

BACKGROUND OF THE INVENTION

Lead has been found to have specific and significant effects on chondrocytes, osteoblasts, and osteoclasts in in vitro and animal models at environmentally relevant levels. However, the implications of these effects in humans remains unclear. Preliminary data suggest that lead reduces bone remodeling, with preferential adverse effects on osteoblasts and growth plate chondrocytes. This argues that lead could cause both a decrease in peak bone mass attainment during childhood, as well as increasing the risk of osteoporosis in adults. Furthermore, since bone is the major repository of lead in the body, under circumstances of enhanced bone resorption there is a serious concern that release of lead could result in increased toxicity to other organ systems. This becomes particularly relevant in the case of postmenopausal osteoporosis, where accelerated bone resorption may elevate blood lead levels.

Research on the adverse effects of high lead exposure in humans has primarily focused on neurocognitive outcomes among children. However, a growing body of literature reports that the effects of childhood lead exposure continue into adolescence and adulthood. These effects include delinquent behavior, dental caries, cardiovascular disease, cardiac arrhythmias, and renal dysfunction. These delayed effects are probably due to the fact that lead is harbored in bone for years after initial exposure, and thus may be a source for later exposure.

The skeleton is the major reservoir of lead in the body and consequently its lead content reflects cumulative lead exposure. However, little is known specifically about the effects of lead on the skeleton and the mechanisms of action through which it may affect bone growth and remodeling. In vitro and in vivo experimental data that demonstrate effects on bone and an association between lead exposure and decreased bone density form the basis for the clinical studies in this project, which can examine the relationship between lead exposure and bone mineral density in populations of school-age children, skeletally mature adolescents, and older adults. Examination of the relationship between bone metabolism and cumulative lead exposure in these three distinct age groups representing different phases of bone mass regulation in humans may provide novel insights, and has not been previously undertaken.

Skeletal Effects of Lead Exposure—In Vitro and Animal Studies

Lead has been associated with both low birth weight and short stature, although there is controversy as to whether this results from specific skeletal effects or is related to systemic and nutritional factors. Substantial preliminary data presented in Projects 1, 2, and 3 demonstrate potent specific effects of low levels of lead on chondrocytes, osteoblasts, osteoclasts, and mesenchymal stem cells. In vitro studies have shown that lead has specific effects on growth plate chondrocytes that alter cell phenotype and function. Also, potent inhibitory effects on osteoblast and osteoclast phenotype and function have been demonstrated, suggesting that lead may have effects on bone development and remodeling. Importantly, lead toxicity at environmentally relevant levels has been shown by our group and others to decrease BMD in rats and produce osteoporosis in other animal models. Thus while systemic effects of lead on other organ systems may influence the skeleton, there appear to be direct effects of low levels of lead on the cells involved in bone development, remodeling, and repair. Examination of the histomorphometry of lead intoxicated rats shows abnormalities of the growth plates, including defective remodeling and altered growth plate thickness with loss of proliferating cells and disorganization of the growth plate architecture. Preliminary data in Project 2 demonstrate that lead accelerates growth plate chondrocyte maturation by modulating critical autocrine growth factors. Thus, lead exposure could potentially lead to premature bony maturation.

Skeletal Effects of Lead Exposure—Clinical Studies

Despite the extensive basic-science research on the effects of lead exposure on bone metabolism, human studies on this association are limited. Laraque found that lead-exposed African-American children had a higher mean mineral content than age-matched, white norms. At age 36-47 month, the mean bone mineral content of the radius of the lead-exposed subjects and norms were 0.268 gm/cm$^2$ vs. 0.215 gm/cm$^2$, respectively (P<0.005). The authors attributed the findings to racial differences in bone density. In further analysis, Laraque plotted age against bone density among children with low vs. high lead exposure (i.e., blood lead level $\leq$29 µg/dL vs. $\geq$30 µg/dL); the difference in bone density was not significant (p=0.63). Laraque concluded that lead exposure is not associated with changes in bone mineralization. However, since the comparison group was made up of children with moderate-level lead exposure (i.e., blood lead level 12-29 µg/dL), such an analysis cannot exclude the possibility that lead exposure has a threshold effect on bone density at lower blood lead levels. A study found a decreased bone density in rats with a mean blood lead level of only 21 pg/dL when compared to control animals.

Although recent studies report a dramatic decrease in the prevalence of lead exposure in the U.S., this does not imply that adults have not had exposure in the past. As recently as the late 1970s, 78% of the entire U.S. population—children and adults—had blood lead levels $\geq$10 µg/dL, the current threshold of concern defined by the Centers for Disease Control. This means that the majority of adults in the U.S. had, at some time in the past, an elevated blood lead level, and therefore currently have elevated bone lead levels, given the extremely long half life of lead in bone ($\tau_{1/2}$=20 yr). With this large number of adults who have elevated bone lead levels, and the morbidity associated with osteoporosis, it is important to investigate whether an association exists between lead exposure and osteoporosis in humans.

This research, however, cannot be limited to adults. Although osteoporosis is an affliction of the elderly, its roots may be established during childhood. An individual who does not achieve peak bone mass during childhood may be at-risk for osteoporosis in later life. Since 90% or more of bone mass is achieved by age 17-20 years, the association between lead exposure and bone density should be examined among children and skeletally mature adolescents.

Bone Mass and Osteoporosis

Osteoporosis is a disease of epidemic proportions in the United States, with an estimated 25 million affected individuals. The health care costs of treatment of osteoporotic hip and spine fractures and associated morbidity may exceed $10 billion per year. During childhood and adolescence, bone mass accretion occurs through both the activities of the chondrocytes in the growth plates and the bone forming activity of osteoblasts. Thus, bone mass and bone mineral density (BMD) gradually increase during growth. Bone mass is a reflection of the relative rates of bone formation and bone resorption, and continues to increase into early adulthood after growth plate closure, until peak bone mass is reached at age 25-30. After peak bone mass is reached, bone resorption rates exceed formation rates, and there is a gradual loss of bone with further aging in both men and women. At menopause, the loss of estrogen results in an acceleration of the rate of bone loss, which occurs over approximately a 10-year period, subsequently slowing to a rate resembling premenopausal bone loss rates. Systemic stimuli of bone resorption, such as corticosteroids, thyroid or parathyroid disease, can further enhance the rate of bone loss. BMD correlates with bone strength and inversely with fracture risk. As bone is lost, an individual can cross a theoretical "fracture threshold" where the BMD and associated bone strength are insufficient to resist nontraumatic forces on the bone and can lead to fractures. Men achieve greater peak bone mass levels and are not subject to the accelerated decline associated with menopause, so bone density levels are less likely to cross the fracture threshold, explaining the 5-6-fold higher incidence of osteoporosis in women as compared to men. Also there are other genetic determinants of bone mass such as race. Black men and women have been shown to have higher peak bone mass compared with white and Hispanic individuals, thus accounting for the decreased incidence of osteoporosis among blacks. Antiresorptive treatments such as estrogen, estrogen analogs, and bisphosphonates at menopause have been shown to prevent accelerated bone loss and reduce fracture risk in perimenopausal women. The inhibitory effects of lead on chondrocytes and osteoblasts could result in attainment of a lower peak bone mass, predisposing lead-exposed individuals to osteoporosis later in life. Furthermore, lead released from bone matrix during increased resorption, such as at menopause, could increase local concentrations at bone surfaces, worsening the inhibition of osteoblastic bone formation, and therefore accelerating the loss of bone by further disturbing the balance of bone formation and resorption. Osteoporosis associated with lead intoxication has been previously reported, consistent with our own findings and those of others with animal models of lead toxicity causing osteopenia.

Systemic Toxicities of Skeletal Lead

Because bone has been shown to be the repository for 90-95% of lead in the body, there has been significant concern that release of lead from bone during menopause could lead to elevated blood levels and significant toxicity. A study of blood lead levels in Hispanic women demonstrated higher blood leads in women within the first 4 years of menopause as compared to women who were more than 4 years postmenopausal, supporting this concern. Similarly, data from the National Health and Nutrition Examination Survey II (NHANES II, 1976-1980) demonstrated a significant increase in blood leads following menopause. Further support for this observation was presented in a prior study of antiresorptive therapy with estrogen in lead-exposed women by Webber et al (1995). He showed that bone lead was significantly higher in women treated with estrogen than in the untreated group. More potent antiresorptive agents such the bisphosphonates, alendronate or risedronate, which are now standard therapies for postmenopausal osteoporosis, have not been studied with regard to effects on lead metabolism.

Numerous other conditions of accelerated bone resorption have been shown to increase blood lead levels, including immobilization, thyrotoxicosis, and hyperparathyroidism. The significance of the accelerated release of lead from bone in postmenopausal women relates to the known toxicities of low levels of lead on other organ systems, such as the central nervous and cardiovascular systems. Lead intoxication at low levels has been associated with hypertension in both children and adults, and has been shown to cause cognitive dysfunction in older adults. Elevated lead levels have been reported after immobilization for a fracture, with associated renal toxicity in one report. This has added clinical significance given data that demonstrate lead-related abnormalities of fracture healing. Local elevation of extracellular fluid lead levels at a fracture site secondary to increased resorption from the combined inflammatory response and immobilization could impair or delay the healing of osteoporotic fractures. The data on systemic toxicities of bone-derived lead form the basis for the proposed clinical trial of alendronate in lead-exposed menopausal women to determine if a potent antiresorptive can prevent the rise of blood lead during accelerated bone resorption.

Measurement of Bone Lead

The method of K shell X-ray Fluorescence (KXRF) has been employed to measure bone lead in occupationally lead exposed and unexposed individuals. In vivo bone lead measurements were first developed by Ahlgren and Mattsson at Lund in Sweden. They used X-rays from a $^{57}$Co source to excite lead K shell electrons. Measurement was made in a finger bone and this system has been in operation since 1972. Subsequently, an improved system was developed by Chettle, Scott, Laird and Somervaille in Birmingham, England. This system used X-rays from a $^{109}$Cd source to excite the lead K electrons to produce gamma rays (i.e., X-ray fluorescence), and proved to have three particular advantages over the original approach: measurements were more precise; bone lead content could be directly related to bone mineral; and measurements could usefully be made of any superficial bone. The first human measurements were made in 1983 and initially the tibia lead concentration was studied. Since then the calcaneus has frequently been selected as a trabecular bone site. The patella has also been used in this way, and measurements have also been reported of radius, sternum and skull. This measurement approach has been adopted by a number of laboratories around the world. In 1991, Chettle and Webber at McMaster University developed a new system, with improved precision, based on the same principles.

Two particular features of the relationship between bone lead and lead exposure have consistently emerged from studies in which K X-ray fluorescence technology has been employed. First, bone lead concentration reflects cumulative lead exposure. Cumulative exposure can be represented by the time-weighted integral of blood lead, monitored regularly in lead exposed workers. Secondly, release of lead from bone contributes to circulating lead in blood, thus constituting an endogenous exposure. This relationship is particularly clear when industrial exposure has ceased. For such people, endogenous exposure can often be the dominant contributor to current blood lead.

SUMMARY OF THE INVENTION

Some aspects of the invention involve a method of correcting a bone density value for an effect of lead, the method including determining an apparent bone density in a patient; applying a correction factor to the apparent bone density, the correction factor being based on a lead level; and deriving a corrected bone density value for the patient.

In some embodiments, the lead level includes a blood lead concentration, and both the apparent bone density and the blood lead concentration are measured in the same patient. In other embodiments, the lead level includes a bone lead level, and both the apparent bone density and the bone lead level are measured in the same patient. In some embodiments, the lead level is an average lead level in a population.

In some embodiments, the bone lead level is determined by x-ray fluorescence, such as K shell x-ray fluorescence, as is known to those of skill in the art. In certain embodiments, the x-rays in the K shell x-ray fluorescence are emitted from a $^{57}$Co source.

In some preferred arrangements, the determining of an apparent bone density includes making a dual-energy x-ray absorptiometry measurement of a bone in the patient. In some embodiments, the bone is a calcaneus. In certain preferred arrangements, the determining of an apparent bone density includes making an ultrasound measurement of a bone in the patient.

In some aspects of the invention, the correction factor is applied to the apparent bone density according to the equation: corrected bone density=apparent bone density×(A(blood lead level)+B)/B. In some embodiments, A is about −1, about −1.08, and/or about −1.075. In some embodiments, B is about 170 to about 180, about 175, and/or about 175.4.

DETAILED DESCRIPTION OF EXEMPLARY EMBODIMENTS

Given the potent effects of low levels of lead on bone and cartilage cells and the widespread exposure of the adult population of the U.S. to lead historically, lead may be an unrecognized contributing factor in the current and expanding epidemic of osteoporosis in this country. Skeletal effects of lead during childhood could predispose to osteoporosis by diminishing achieved peak bone mass through acceleration of bony maturation, consistent with the observed effects of lead on growth plate chondrocytes. The release of skeletal lead during menopause could also contribute to neurocognitive, cardiovascular, or other systemic toxicities. The proposed studies represent the first comprehensive analysis of the relationship of bone lead to bone density in children, skeletally mature adolescents, and older adults. In addition this can be a test of a potent antiresorptive agent to evaluate its therapeutic value in lead-exposed menopausal women. Finally, the documentation of a lead-related artifact in DEXA measurements could revolutionize the interpretation of DEXA results, and mandate knowledge of an individual's lead exposure or bone lead content in order to ensure accurate use of this highly prevalent testing and screening modality. Thus the project has tremendous clinical significance, with potential to (1) expand the understanding of the role of a common environmental toxin in the context of a potentially epidemic disease (osteoporosis); (2) identify critical new caveats in testing interpretation for this disease; and (3) evaluate the utility of a new therapeutic intervention.

Lead and DEXA Measurement Artifact

The skeletal data on rats with lead exposure is somewhat controversial. Gruber et al (1997) demonstrated that lead caused a decrease in bone mass by DEXA, histomorphometry, and mineral analysis. In a subsequent study, the effect of lead exposure was ameliorated by calcium supplementation. Lead exposed rats have been also shown to have decreased femoral weights and L5 vertebral body heights, as well as histomorphometric evidence of osteopenia. However, the bone density in this study as measured by DEXA was higher in the lead treated animals. This is consistent with data in our laboratory, dictating that bone samples doped with increasing quantities of lead have spuriously high BMD with a direct dose response effect when measured by DEXA, an artifact which may be related to interactions of the low energy photons of the DEXA with lead atoms causing secondary effects. The magnitude of the effect far outweighs the calculated effect of lead on mineral density, which would theoretically be too small to be measurable. We compared bone densities as measured by DEXA with measurements of bone density by ultrasonography, which estimates bone stiffness, a parameter that is proportional to BMD. However with ultrasound, interactions of the photons with lead atoms are eliminated. If the artifact occurs in measurements of BMD by DEXA in humans, there may be serious implications in the interpretation of clinical DEXA data, which may necessitate knowing an individual's bone lead content to correct for this problem. Preliminary clinical data indicate a significant ($p<0.05$) inverse relationship between blood lead and the ratio of the two densitometric measurements (BMD measured by ultrasound divided by the BMD measured by DEXA), in a pilot study of 13 subjects, which supports our contention that DEXA of lead-containing bone overestimates its density. This finding may also explain the discrepancy reported by Escribano et al (1997) between the histomorphometric data, which indicated osteoporosis in lead-treated rats, and DEXA densitometric data, which showed higher BMD in the same animals.

Aspects of the invention implicate the relationship between lead exposure and bone density in two clinical studies. One can conduct studies in a cross-sectional evaluation of the relationship of bone density and blood lead levels in pediatric patients. One can study the relationship of bone density, bone lead, and blood lead in a population of adults, and can compare the effects of antiresorptive treatment with a bisphosphonate vs. placebo in a controlled prospective manner to determine (1) if treatment of lead exposed subjects decreases bone loss as it does in otherwise normal osteoporotic subjects, and (2) if a potent antiresorptive treatment can prevent systemic release of lead from bone.

First, we have identified populations of low and high lead-exposed pediatric patients, and can evaluate in these populations the relationship between lead exposure as judged from bone lead levels (measured by K-shell X-ray Fluorescence (KXRF), and bone density as measured by dual energy X-ray absorptiometry (DEXA) at specific sites, and with whole body analysis. We can also measure bone density by ultrasound at the calcaneus to correlate with the DEXA measurements and test our finding that bone density measurement by DEXA is falsely elevated by the presence of lead in bone.

Second, we have three specific large cohorts of lead exposed or potentially exposed adults in our region, and can use these populations to study the relationship between bone density and lead exposure. One can identify lead-exposed adults using historical blood lead data and conduct new measurements of bone lead using the KXRF. We can measure bone density by DEXA and ultrasound, as well as selected parameters of bone metabolism. The study groups can be sex and race-matched and stratified into high and low bone lead groups for comparison. Perimenopausal female subjects from the same patient population can be randomized to treatment with alendronate, a potent antiresorptive bisphosphonate used for treatment of osteoporosis, or placebo. We can follow serial blood and bone lead measurements as well as bone density measurements by both ultrasound and DEXA. The questions to be answered are (1) Does bisphosphonate treatment result in a decrease in blood lead levels and an increase in retention of bone lead? and (2) Do subjects with lead contaminated bone respond to bisphosphonate treatment with a decrease in bone loss as occurs in otherwise normal osteoporotic bone? We can also evaluate the comparative measurements of bone density by DEXA and ultrasound as a function of bone lead to provide further data evaluating the possible artifactual effects of lead in bone density determinations.

We have uncovered a potentially serious artifact for the measurement of bone mineral density in patients with lead in their skeletons. In fact, the extent of this problem could pervade all density measurements and necessitate that we re-examine the algorithms for correlating density with fracture risk. Simply put, unless one knows the bone lead content of patients being measured by DEXA, an accurate BMD cannot be determined.

Given the toxicity of lead; the sequestration of lead in bone; and the availability of dual energy x-ray absorptiometry (DEXA) it is surprising that many more articles have not appeared in the literature documenting low bone density in patients and animals exposed to this heavy metal. Rather, examination of some of the national health survey data bases suggests that DEXA bone mineral density measurements may actually be slightly higher in lead exposed individuals. Yet the weight of evidence supports an adverse effect of lead on osteoblasts, osteoclasts chondrocytes and animal bone metabolism. How can this issue be resolved?

Lead interferes with the DEXA analysis itself. In order to test this we performed control experiments measuring bone mineral densities in bovine bone samples to which were added trace amounts of lead. The actual data appear in FIG. 1. We found that very small amounts of lead interfere with DEXA measurements of bone density. In fact, at bone lead levels in the physiological range, it appears that DEXA overestimates bone density by 4-11 percent. The real mechanism for this artifact is not known, however, it is likely related to the behavior of a low energy x-ray in the vicinity of a heavy metal atomic nucleus. In work published by Kramer and Webber in 1994 (Appl. Radiation and Isotopes 45: 749-752) it was shown that gamma rays from a dual photon absorptiometer (DPA) were differently absorbed depending on the content of high atomic number elements. They quote "the apparent . . . density . . . depends upon the product of the mass of the element in the beam and upon a factor which is a complicated function of the mass attenuation coefficients for the element concerned."

This is the first suggestion that DPA (and presumably DEXA) could not accurately measure tissue density without correcting for the composition of the tissue.

In order to determine if the artifact is present in patients we measured bone mineral density in ways that would not be affected by skeletal lead levels (i.e. with ultrasound). Comparing these results to a DEXA determination at the same site in the same patient should provide evidence that the artifact is clinically relevant. The preliminary data are presented in FIG. 1.

Figure 1:
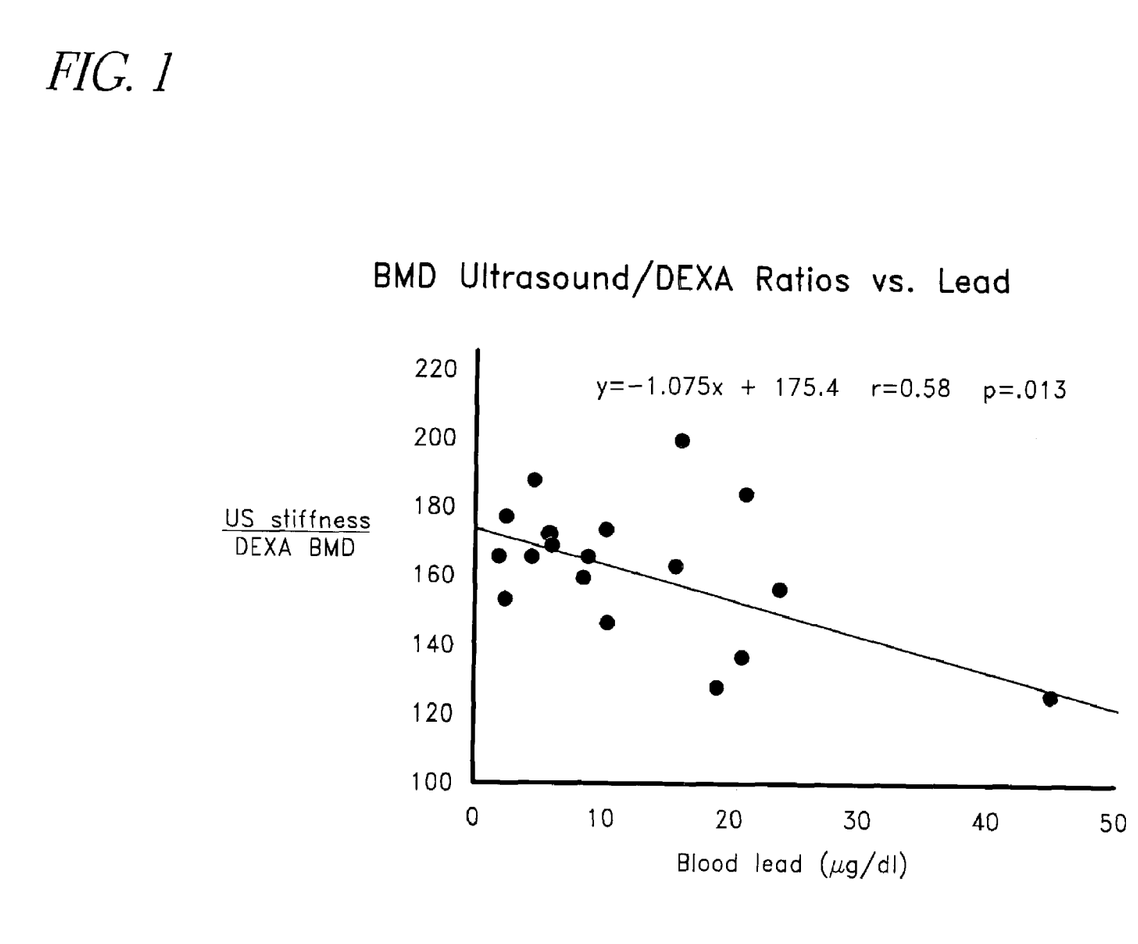
FIG. 1 is graph of blood lead concentration versus ultrasound measurement of bone stiffness relative to DEXA determination of bone mineral density.

These results show that the ratio of bone density as determined by ultrasound to that determined by DEXA (i.e. US/DEXA) trends downward with increasing concentrations of lead exposure. That is, if neither technique were affected by lead in the bone the ratio would remain constant. However, if the DEXA determination is artifactually increasing as bone lead content increases the ratio would tend to decrease. Shortcomings of this analysis are that we are using a static blood lead level as an estimate of bone lead. As we add more patients to this analysis and measure bone lead directly with KXRF, it should be possible to refine these data. Nevertheless, this is the first piece of evidence that indicates that lead may represent a clinical problem in determining an accurate bone mineral density.

The Association Between Dental Caries and Childhood Lead Exposure.

Epidemiological studies suggest an association between lead exposure and caries. The objective was to establish whether children with a higher lead exposure as toddlers had more caries at school age than children with a lower lead exposure. We used a retrospective cohort design. A total of 248 children were examined for caries, and had a record of blood lead levels to define lead exposure. This study demonstrated that lead exposure above 10 µg/dL as a toddler was not a strong predictor of caries among school-age children. It demonstrates the ability of the investigative team to successfully conduct an epidemiological study, much like the one now proposed.

The Association Between Lead Exposure and Decreased Bone Density in Adults in a NHANES III Analysis.

The objective was to conduct a secondary analysis of a national database to explore the association between blood lead level and osteoporosis in adults. We used data from the Third National Health and Nutrition Examination Survey (NHANES III) (NCHS, 1994). We defined a subject's past lead exposure by their concurrent blood lead level. BMD measurements were obtained using DEXA instruments (Hologic QDR 1000, Waltham, Mass.). The anatomic sites examined were the femoral neck, trochanter, intertrochanteric area, and total hip (NCHS, 1994). We wished to define a population of adults without secondary osteoporosis. The age was restricted to subjects $\geq 50$ years; we excluded subjects who reported having a medical condition that either affected bone density or predisposed to immobilization, or reported taking medications that adversely or beneficially affect bone density. The remaining subjects made up the primary sample, which underwent analysis. Covariates considered were socioeconomic status, tobacco use, ethanol consumption, physical activity, body mass index (BMI), past calcium intake, race, and sex.

Because race and sex are strongly associated with bone density, we conducted separate analyses on four groups: white men, white women, African-American men and African-American women. For each of these four groups, we analyzed the BMD at each of the four anatomic sites of the femur (i.e., neck, trochanter, intertrochanteric, and total hip). To define potential confounders for adjusted analysis, we conducted bivariate analysis (for each age- and sex-defined group) between the covariates described above, and the total hip BMD. The covariates were introduced into multiple ANOVA (MANOVA) to determine the independent association between BMD and blood lead level tercile. We used SUDAAN software to estimate confidence intervals that accounted for the multi-stage sampling design of the survey.

A total of 634 subjects were white men, 309 were white women, 249 were African-American men and 151 were African-American women. We identified the following covariates as significant in bivariate analysis: white males—age, BMI and education level; African-American males—age, BMI, education level, and cigarette consumption; white females—age, BMI, and cigarette consumption; African-American females—age and BMI. The adjusted mean BMD revealed only one comparison that was significant: the mean total hip BMD among the white males with a high-range blood lead level tercile versus those with a low-range blood lead tercile (0.944 gm/cm$^2$ vs. 0.974 gm/cm$^2$, respectively; P=0.05). Another comparison, the mean trochanter BMD among the white males with a high-range blood lead level tercile versus those with a low-range tercile, was marginally significant (0.721 gm/cm$^2$ vs. 0.747 gm/cm$^2$, respectively; P=0.09). These data provide the first evidence of an inverse relationship between bone density and lead in a population study of adult humans.

There are several limitations to this study. Although significant associations were not noted among white females, African-American females or African-American males, the sample size of each of these groups were smaller than the group of white males, thus decreasing statistical power. Further, the mean blood lead level among the white males was higher than among either female group, suggesting that the lack of an association among the females may be due to subtoxic lead exposure. The possible lead-related artifactual elevation of the DEXA values has also not been taken into account in this analysis. Finally, the significant association found in this study is more plausible when considering this same association was noted in animal studies. In light of these limitations, further inquiry is necessary into the possible association between lead exposure and decreased bone density.

The Effect of Lead Exposure on Bone Density in Children

Our objective was to derive pilot data regarding the association between lead exposure and bone density in children. The initial hypothesis was that the bone density of children with high lead exposure would be lower than the bone density of children with low lead exposure. We used a cross-sectional design. We enrolled children age 8-10 years. Children with a past history of elevated blood lead levels were recruited from a local clinic for lead exposed children (Lead Poisoning Prevention and Treatment Center, Rochester General Hospital, Rochester, N.Y.). Children with lower blood lead levels were recruited from an urban pediatric practice (Rochester General Pediatric Associates, Rochester General Hospital, Rochester, N.Y.). We excluded children who had medical conditions that affect bone density (i.e., sickle cell anemia, osteogenesis imperfecta), who use certain medications that affect bone density (corticosteroids, anticonvulsants, diuretics), or who have evidence of sexual maturation (i.e., Tanner Stage$\geq$II).

We defined lead exposure as the arithmetic mean of venous blood lead levels collected during four age periods: 13-24 months, 25-36 months, 37-48 months, 49-60 months. Subjects were defined as having a high lead exposure if this measure was $\geq$15 pg/dL, or as having low lead exposure if this measure was <15 μg/dL. We used a DEXA scanner (Prodigy Scanner, Lunar Corp., Madison, Wis.) to measure BMD at multiple regions. In addition, BMD was measured by an ultrasound instrument (Achilles Express Ultrasonometer, Lunar Corp., Minster, Ohio) at the calcaneus. We matched each subject with high lead exposure to a subject with low lead exposure on age ($\pm$12 months), race, and weight ($\pm$7 kg.). We also collected measures of physical activity and calcium intake.

We have collected data on 28 subjects. All were African-American. Nine had low lead exposure (mean 5.8 μg/dL; range 2.7-10.3 μg/dL) and 19 had high lead exposure (mean 23.6 μg/dL; range 15.5-43.5 μg/dL). There was no difference between these groups on age, sex distribution, weight, body mass index, calcium intake, physical activity or socioeconomic status. Out of 30 comparisons of bony sites for BMD, we found 15 that were significantly different (P$\leq$0.05). However, contrary to our hypothesis, we found that subjects with high lead exposure had a higher BMD based on DEXA measurements than subjects with low lead exposure. The most pertinent findings are tabulated below.

| Site | BMD-Low Lead | BMD-High Lead | P-value |
| --- | --- | --- | --- |
| Head | 1.580 | 1.720 | 0.014 |
| Trunk | 0.670 | 0.718 | 0.005 |
| Rib | 0.578 | 0.615 | 0.006 |
| Pelvis | 0.775 | 0.836 | 0.031 |
| Spine | 0.688 | 0.747 | 0.016 |
| L1–L4 | 0.701 | 0.769 | 0.040 |
| Left Fem Neck | 0.785 | 0.886 | 0.030 |

These findings indicate that high lead exposure is associated with higher bone density. Inconsistent with these findings are animal-based studies that have found an inverse association between lead exposure and bone mass determined by histomorphometry.

FIG. 1 is a graph of blood lead concentration versus an ultrasound measure of bone stiffness relative to (divided by) a DEXA determination of bone mineral density. As FIG. 1 shows, as blood lead concentrations increase, DEXA BMD measurements decrease for a given ultrasound stiffness value. This occurs at a slope of about 1.075. Linear regression analysis reveals the relationship between blood lead levels and U.S. stiffness/DEXA BMD to be y=−1.075x+ 175.4. For these findings the correlation coefficient is 0.58 and the p value (probability that the results achieved could have occurred by chance) is 0.013.

Figure 2:
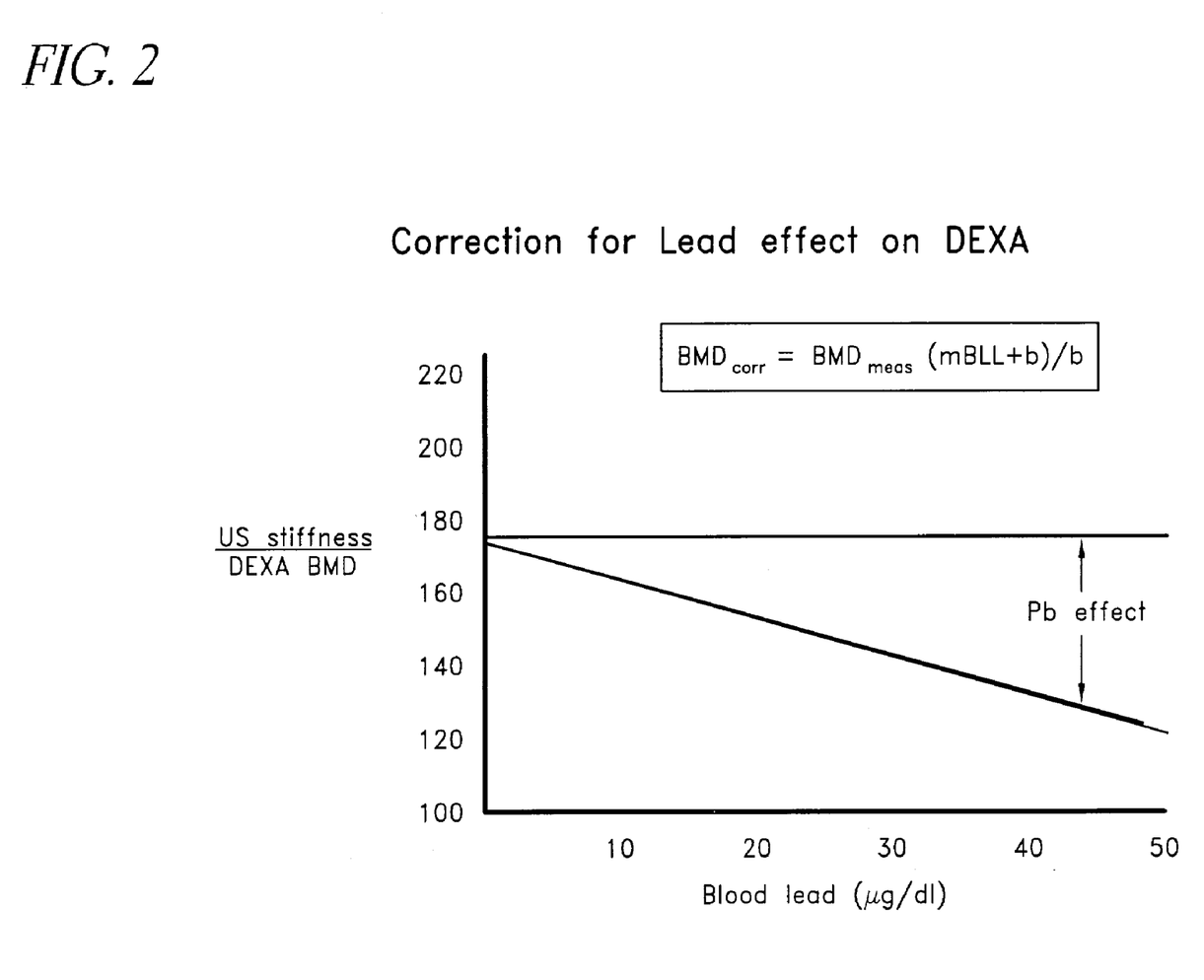
FIG. 2 is a graph displaying blood lead concentration versus ultrasound measure of bone stiffness relative to DEXA measurement of bone mineral density, including a correction for lead effect on DEXA.

FIG. 2 shows the relationship between blood lead concentrations and ultrasound stiffness relative to DEXA BMD measurements. The lead (Pb) effect is shown by the space between the two lines on the graph. The upper line represents a constant DEXA BMD, i.e., that which would occur without the presence of lead; and the lower line represents the effect on DEXA BMD by increasing blood lead concentrations.

Figure 3:
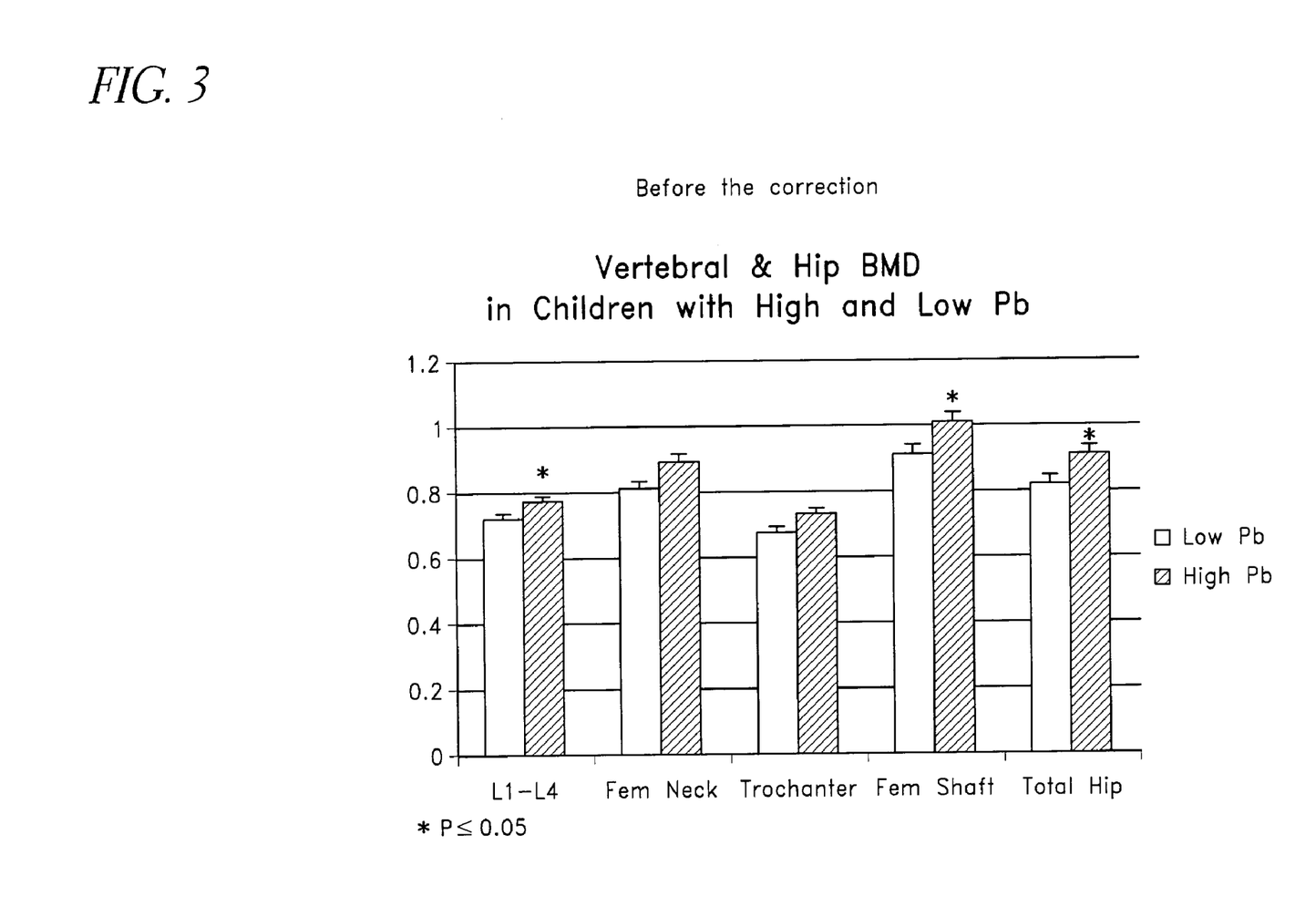
FIG. 3 shows a graph of vertebral and hip bone mineral density in children with high and low body blood levels.

FIG. 3 shows the bone mineral density in children with high and low body blood levels for those bones, including the lumbar spine, femoral neck, greater trochanter, femoral shaft, and total hip. With a P value of $\leq$0.05, this shows statistical significance in the difference in bone mineral density (BMD) between high lead and low lead levels.

Figure 4:
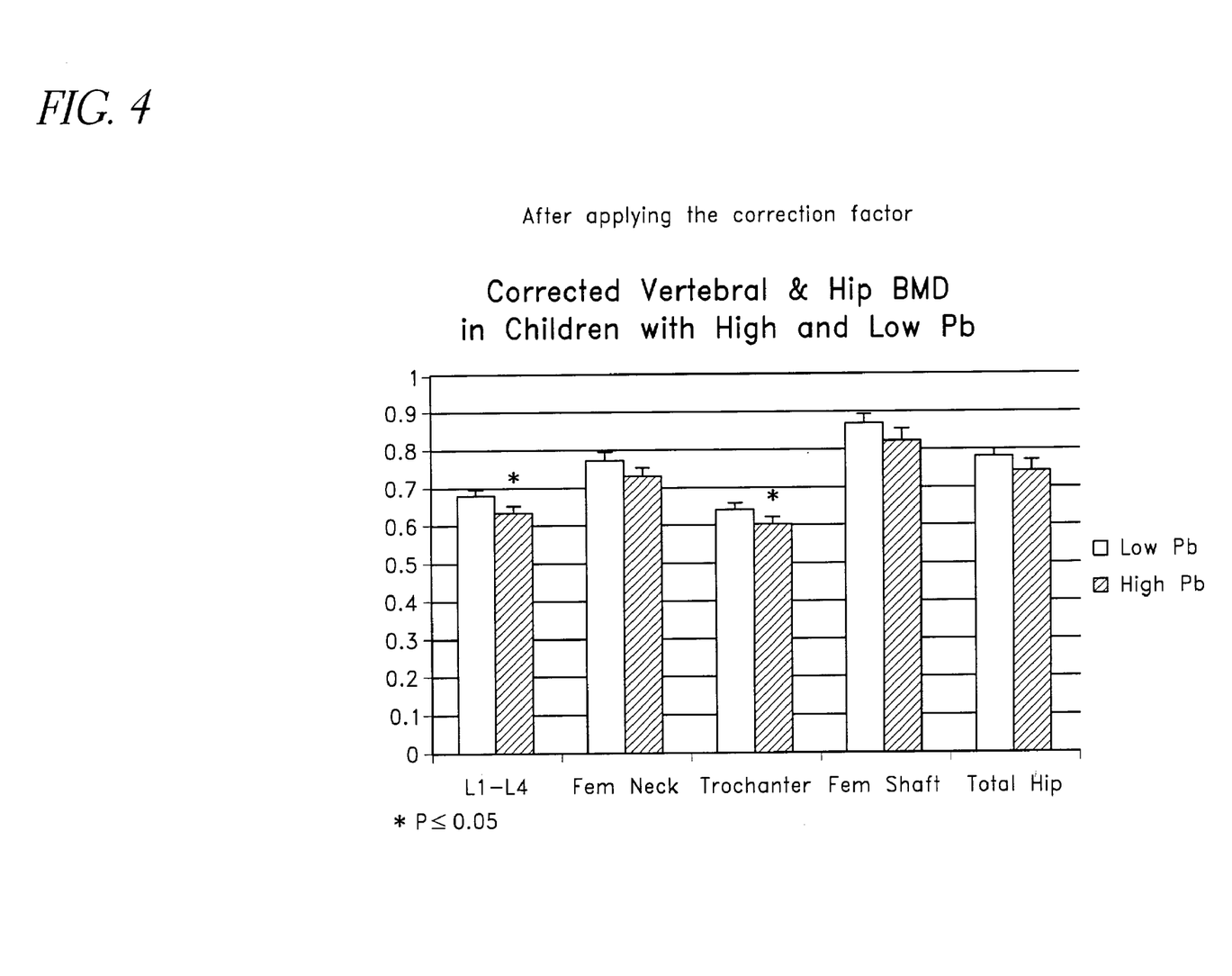
FIG. 4 shows a graph of corrected vertebral and hip bone mineral density in children with high and low body blood levels, after applying the correction factor.

FIG. 4 shows corrected vertigo and hip bone mineral density (BMD) measurements in children with high and low blood levels. After applying the correction factors, it is seen that the DEXA bone mineral density decreases significantly, indicating an artificial increase in bone mineral density (as measured by DEXA) that results from the effective lead atoms in bone.

The effects of lead on chondrocytes suggest that lead accelerates chondrocyte maturation, similar to the defects seen in murine deletion models of PTHrP or its receptor. Thus lead exposure may lead to advanced skeletal maturity. Therefore skeletal age, determined by ossification patterns on conventional AP radiographs of the wrist in children, may be greater than the chronological age in lead exposed children. This would lead to a higher bone density in relationship to age-matched bone used in interpretation of DEXA scans, which is based on chronological age only. One report has documented systemic acceleration of maturity by lead toxicity, although animal studies have suggested a decrease in sex steroids associated with lead toxicity. However, the effect of lead in accelerating skeletal maturation may not be an indirect hormonal effect but could be a direct effect on the skeleton independent of sexual maturation. The accelerated skeletal ossification could cause an apparent increase in bone density during growth as related to chronological age, but still result in a lower peak bone mass and therefore a predisposition to osteoporosis later in life. We can analyze bone density as a function of bone age in the pediatric subjects to examine this possibility. To our knowledge this has not been previously analyzed in pediatric bone density studies, and published normative data has been derived only from chronological age.

An alternative (or additive) explanation for our paradoxical finding is that lead in bone causes an artificial increase in bone density when measured by DEXA. Escribano found, as in our study, that bone density measured by densitometry was higher in high lead exposed rats than controls. However, the "gold standard" histomorphometric measures of bone density (i.e., trabecular bone volume, trabecular number, and trabecular thickness) were lower in high lead exposed rats than controls. Escribano speculated that the lead-associated increase in bone mass, as measured by DEXA densitometry, could due to the lead in bone. This phenomenon of a false-elevation of BMD occurs in bone containing strontium. Edward Puzas, PhD, in an in-vitro study, has found evidence that this phenomenon may occur when bone contains even minute quantities of lead. The bone lead content we would expect in our pediatric lead-exposed patients as judged from their blood lead histories could cause an artifactual elevation of DEXA values by 4-11% according to our in vitro studies of this phenomenon. BMDs in our pediatric population corrected for the hypothetical acceleration of bony maturation and the overestimate of BMD by DEXA due to the lead artifact could readily decrease the BMD values in high lead exposed subjects by 10-15%, which would actually reverse the trends seen in the preliminary study. The density values in the high lead group shown in the above table ranged from 6.4% to 9.7% above the controls.

As an alternative to a DEXA-based BMD measure, we conducted ultrasound-based BMD measure of the calcaneus in the pediatric subjects. We found no difference between low lead exposed and high lead exposed subjects (81.6 vs. 85.2, respectively; P=0.561). Moreover, when the ultrasound density values and DEXA density values were plotted as a ratio (US/DEXA) versus lead exposure, a statistically significant inverse relationship was identified, indicating that the DEXA values increased with increasing lead, whereas the ultrasound density determinations did not. This provides supporting evidence for the existence of a lead-induced artifact in the measurement of bone density by DEXA. Limitations of the pilot study include the racial composition of African Americans, examination of only the calcaneal site by ultrasound without bone lead measurements of that specific site, and the fact that the young age of the children in the study may not have allowed enough time for the lead effects on bone to become fully manifested.

Due to the ability of DEXA-based instruments to measure BMD at all bony sites, this technology is preferable. Fortunately, the in vitro studies by Dr. Puzas may provide a way to correct for this false-elevation, if confirmed by further data in the studies of this project. Proposed studies can assess children of at-risk races (i.e., whites), and at older ages. In addition, KXRF measurement of lead bone concentration should enable us to correct for this apparent false elevation of BMD. These important questions underscore the value of obtaining the proposed clinical data to help define the effects of lead on the skeleton.

Study to Determine the Number of Potential Subjects in Rochester, N.Y.

Given the limitations of the pilot study specified above, our proposal is to study subjects at two age cohorts (8-9 years, and 18-19 years), and among white populations as well as African-American populations. We therefore conducted a study to determine the number of potential subjects available in Rochester.

A subject's cumulative lead exposure can be defined as their tibia bone lead level. Twenty-seven percent of 1-5 year-old children have elevated blood lead levels ($\geq 10$ μg/dL) in Monroe County. Previous studies report a good correlation between cumulative blood lead levels and bone lead levels in adults, and we assume the same is true in children.

We identified the number of children who had an adequate number of blood lead screening levels (at least one blood lead level during ages 12-23 months, 24-35 months and 36-48 months for children born in 1993) to define past lead exposure from a comprehensive database from the Monroe County Health Department. We did not examine blood lead levels beyond age 48 months because only 0.6% of children with a history of an elevated blood lead level had their first elevation after age 48 months (James Campbell, MD, MPH, unpublished data, July 2001). We identified 760 children born in 1993 who fit the aforementioned criteria; 347 (46%) of these children are registered at the pediatric clinic at Rochester General Hospital or Strong Memorial Hospital, clinics where Dr. Campbell has access to the charts. Among these 347 children, 57% were male. The mean of all blood lead levels for ages 1-3 years was 8.9 μg/dL, with 69% 0-9 μg/dL; 27% 10-19 μg/dL.; and 4% $\geq 20$ μg/dL.

We next defined the number of 19-year-old adolescents (born in 1983) with an adequate number of blood lead levels to define past lead exposure using similar methods and database. We identified adolescents who had at least one elevated blood lead level (i.e., $\geq 10$ μg/dL) between ages 9-72 months. Among this cohort, we calculated the mean of all blood lead levels during this age span. We identified 133 adolescents born in 1983 who fit the aforementioned criteria. The distribution of mean blood lead levels is as follows: 0-9 μg/dL—32%; 10-19 μg/dL—4%; 20-29 μg/dL—18%; 30-39 μg/dL—34%; $\geq 40$ μg/dL—12%.

There are many 9-year old children who attend Dr. Campbell's clinics, and are therefore potentially enrollable. Further, the mean blood lead level of these potential subjects ranges from very low to moderate. This broad range of the independent variable of interest is critical to allow the analysis we propose. The 19-year old cohort is predominantly made up of subjects with a past history of high lead exposure, and our analysis indicates an adequate number of available subjects.

We hypothesize that subjects who have high lead exposure can have lower BMD than subjects who have a low lead exposure, when effects on acceleration of skeletal maturation and the lead-related artifactual elevation of DEXA-measured BMD are taken into account. A corollary hypothesis is that the bone age can be higher in high lead exposed skeletally immature 8-9 year-old subjects than in low lead exposed subjects, reflecting an acceleration of bone maturation. The association between BMD and bone lead level can be examined among the following groups: White 8-9 year-olds, African-American 8-9 year-olds, White male 18-19 year olds, African-American male 18-19 year olds, White female 18-19 year olds, African-American female 18-19 year olds.

We hypothesize that 18-19 year-old subjects who have higher lead exposure can have lower measures of both bone resorption (i.e., urinary type I collagen N-telopeptides) and bone formation (i.e., alkaline phosphatase, serum osteocalcin) than subjects who have lower lead exposure. This would reflect parameters consistent with low turnover osteoporosis, as is observed with the example of chronic steroid use.

We hypothesized that bone mass in 18-19 year-olds, which approximates peak bone mass, is lower in subjects with high lead exposure than subjects with low lead exposure.

We can determine if lead in bone causes an artificial increase in bone density when measured by DEXA. We hypothesized that subjects who have a high lead exposure have a higher BMD by DEXA, and lower BMD by ultrasound than subjects who have a low lead exposure.

We based the sample size on a two-tailed comparison of means. With every unit of standard deviation that BMD falls below the mean, the risk of osteoporotic fracture doubles. We concluded that the clinically relevant difference of BMD to be a unit decrease of one standard deviation. The absolute value of the standard deviation is irrelevant. The sample size calculation depends on the ratio of the assumed difference between the two means and the pooled standard deviation. Since we assume the clinically relevant difference is one unit of standard deviation below the mean, the ratio will always be 1, regardless of the size of the standard deviation. We selected a two-sided α-error to be 5%, and selected a power $(1-\beta)$ of 90%.

The sample size for each race-, age- and sex-defined group is 44. Half of the subjects can have high lead exposure and half can have low lead exposure. Given six groups are needed, a total of 264 subjects are required.

We use a Prodigy DEXA scanner (Lunar Corp., Madison, Wis.) to measure bone mineral density (BMD). DEXA systems use two x-ray beams, one at a higher energy and one at a lower energy. After subtraction of soft tissue absorption, the attenuation of each x-ray beam by bone is used in calculating the BMD. The BMD can be determined at the hip, spine, calcaneus, and total body; the latter allows analysis of any number of additional specific regions such as ribs, skull, long bones, etc. The safety of this measure is discussed below.

Due to the possibility that lead in bone causes an artificial increase in BMD when measured by DEXA, we also use ultrasound technology (Achilles Express Instrument) to measure BMD at the calcaneus. The safety of this measure is discussed below.

Subjects have bone lead levels measured at the patella, calcaneus, and mid-shaft of the tibia with K-shell X-ray fluorescence (KXRF). Lead exposure is defined as the mid-shaft tibia bone lead level. A KXRF cortical bone lead level—such as at the mid-shaft of the tibia—is the most valid measure of cumulative lead exposure since it is highly correlated to serial blood lead levels. This may be because cortical bone is metabolically less active than trabecular bone.

We can also obtain KXRF measurements of primarily trabecular bone sites (patella and calcaneus). The calcaneus can be measured so that we have correlated measures of BMD by DEXA and ultrasound as well as bone lead measures from a single site. This provides the best opportunity for us to document the existence of a lead-related BMD artifact when using DEXA. Measurement of the lead content at trabecular bone sites can also be valuable in determining if there are differential effects of lead on the BMD of cortical vs. cancellous bone. Our expectation is that effects of lead may be greater on more metabolically active trabecular bone.

A great advantage of KXRF is that we are not limited, as in our pilot study, to subjects who had an adequate number of blood lead levels collected in their past. The safety of this measure is discussed below.

The 8-9 year-old subjects can have an AP wrist radiograph to determine bone age, which should be done by an experienced pediatric radiologist. Bone age is not measured on 18-19 year-old adolescents. The bone age can be determined using Tanner-Marshall criteria.

We can determine markers of bone formation and resorption on the 18-19 year-old subjects. We do not perform phlebotomy on the 8-9 year-old subjects because of the potential of limiting accrual due to parental concerns about a painful procedure. The measures of bone metabolism to be obtained include serum calcium, phosphate, 1, 25-dihydroxyvitamin D3 and 25-hydroxyvitamin D3 levels, parathyroid hormone (PTH), bone-specific alkaline phosphatase, osteocalcin levels and urinary N-telopeptides of type I collagen. These assays are all performed as standard laboratory tests through the clinical laboratory services at Strong Memorial Hospital, or they are sent to commercial labs for analysis. We currently perform these measurements routinely in evaluating patients seen in the Osteoporosis Center at The University of Rochester.

The major conditions that affect bone density, and therefore are potential confounding variables, include age, race, sex, tobacco use, ethanol ingestion, presence of certain medical conditions, use of certain medications, weight, physical activity, and calcium intake. Pregnancy mobilizes lead from bony stores, and therefore may lead to an underestimation of bone lead level.

Because age and race are strongly related to bone density, we can match subjects on age and race. Bone density does not vary by sex among children <13 years of age, and therefore the groups of 8-9 year-old children do not have to be matched by sex; conversely, the 18-19 year-old groups need to be sex-matched.

Tobacco and ethanol consumption are associated with an increased risk of osteoporosis. To ensure data collection on potential confounders, we can inquire about smoking and ethanol use at the assessment interview. However, because tobacco and ethanol are weak risk factors in adults and have not been shown to be risk factors in children, we do not exclude patients from the studies on this basis.

The presence of certain medical conditions and the use of certain medications affect bone density. At the time of the assessment interview, we can ask if the potential subject has any medical problems or use any medications. We can exclude subjects who have those medical conditions or who use those medications.

Obesity is strongly associated with a decreased risk of osteoporosis. To minimize the variance of this covariate, we can review the charts of potential subjects for weight and height. From this, we can calculate the body mass index (BMI) (weight [kilograms] divided by the square of the height [meters]. Subjects who have a BMI that is not within 1.5 standard deviations of the mean for their age and sex are not be called for an assessment interview. In addition, among subjects who are initially assessed for enrollment, weight and height can be measured. Persons who have a BMI that is not within 1.5 standard deviations of the mean for their age and sex can be excluded.

Pregnancy increases bone turnover. At the time of the assessment interview, we can ask if the potential subject if they are pregnant. Pregnant women can be excluded.

On the day of the BMD appointment, the Project Coordinator can administer a questionnaire that can collect data on the remaining covariates—tobacco and alcohol consumption, physical activity and calcium intake. We can use validated questions from the Third National Health and Nutrition Examination Survey (NHANES III) (NCHS, 1994). The Project Coordinator can be blinded to the subject's lead exposure status.

The primary analysis can examine whether the BMD at each bony site is lower for the high lead exposure subjects within each race-, age- and sex-defined group. High and low lead exposure can be dichotomized at the median of the study median tibia bone lead level. Since age, body mass index, calcium intake, and level of physical activity are associated with BMD, any residual imbalance in these covariates can be controlled for by analysis of covariance. Also, we can adjust for the false-elevation of BMD due to bone lead using our preclinical data, if we confirm that the ultrasound and DEXA measurements are discordant as expected. The estimated effect of lead exposure in each group can be obtained from this analysis, together with the two-sided p-value from the associated t-test and the 95% confidence interval. Goodness-of-fit can be examined by the F-test to check for model significance and by plotting residuals from the model. If the residual plots show skew, data can be transformed to ensure that the errors follow approximately the normal distribution with constant variance, as assumed by analysis of covariance.

In addition to analyzing the data for each subgroup separately, secondary analysis can involve combining all data for an overall investigation. This allows us to determine whether different lead exposure effects occur by sex, age, and race; we cannot determine this in separate analyses by groups. We can build a larger model for analysis of covariance that incorporates all relevant predictive variables, including age, sex and race. We can examine the effect of lead exposure after adjusting for BMI, calcium intake, level of physical activity, and the interactions between lead exposure and age/sex/race.

We can compare the mean urine N-telopeptides, alkaline phosphatase, serum osteocalcin, 1,25 Vitamin D and bone age between the low and high lead exposure groups. Two-sided t-tests can be used to detect the difference of means in the outcome measures between low and high lead exposure groups. We can also use analysis of covariance to determine if these differences can be ascribed to differences body mass index or other covariates. Model diagnostic plots can be examined for the normality assumption.

We can examine whether a DEXA-measured BMD is artificially increased. We can use paired two-sided t-tests to check the difference between the measurements by DEXA and ultrasound. By categorizing the difference in BMD when measured by DEXA and ultrasound, we can examine whether the conjectured artificial increase tends to occur in subjects with high lead exposure by using Chi-square tests. In addition, we can plot the ratio of the ultrasound-measured BMD to the DEXA-measured BMD as a function of bone lead level, as was done in the pilot study. Finally, we can correct the DEXA-based BMD using our in vitro approximations and compare the mean corrected BMD by lead exposure using a two-sided t-test.

Clinical studies of the relationship between bone density and lead exposure in adults: This study can use a cross-sectional design to evaluate the association between BMD and lead exposure. Subjects are 50-60 year-olds matched on sex and race. This age range can enable us to evaluate the effects of lead exposure on bone density at the age of accelerated bone loss.

All subjects can undergo DEXA-based and ultrasound-based BMD measurements, and a KXRF-based measurement of bone lead level. In addition, they can have bone metabolic parameters measured including serum bonespecific alkaline phosphatase, calcium, phosphate, parathyroid hormone (PTH), osteocalcin, 25-hydroxy-vitamin D3 and 1,25-dihydroxyvitamin D3 levels. Urinary measurement of N-telopeptides of type I collagen can also be determined as an index of bone resorption rate. Analysis can determine if bone formation rates (bone-specific alkaline phosphatase, osteocalcin levels) are affected by lead and if bone resorption is affected by lead exposure. In addition, there may be effects of lead on vitamin D metabolism, which necessitates examination of the PTH/vitamin D parameters. All measurements in this cross-sectional study can be done at only a single time point.

We hypothesize that subjects who have a higher lead exposure can have lower BMD than subjects who have a lower lead exposure. This can be examined among white/Hispanic males, African-American males, white/Hispanic females, and African-American females.

We can explore the mechanism of the association between lead exposure and bone density. We hypothesized that 50-60 year-old subjects who have higher lead exposure have lower measures of both bone resorption (i.e., urinary type I collagen N-telopeptides) and bone formation (i.e., alkaline phosphatase, serum osteocalcin) than subjects who have lower lead exposure; i.e., parameters consistent with low turnover osteoporosis.

We can determine if lead in bone causes an artificial increase in BMD when measured by DEXA. We hypothesized that subjects who have a higher lead exposure have higher BMD by DEXA, and lower BMD by ultrasound measured at the same site than subjects who have a lower lead exposure. We can document a decrease in ultrasound/DEXA BMD ratios as a function of bone lead content.

The increased rate of bone resorption at menopause can release lead from bone stores, elevating blood lead levels. Higher blood lead levels in adults are associated with hypertension, neurotoxicity, and impaired renal function. A previous study of menopausal women treated with estrogen reported that lead was retained in the bone with this form of antiresorptive therapy. We hypothesize that more potent antiresorptives such as alendronate may have an even greater effect to retain lead in bone. In addition it is unknown if lead-contaminated bone responds to bisphosphonates in a manner similar to otherwise normal osteoporotic bone, in which a decrease in bone loss and frequently an increase in bone density occurs. However, we expect a positive effect of bisphosphonate therapy on bone mass despite presence of lead, since the same lead-exposed patients used in the estrogen vs. bone lead study of Webber (1995) exhibited an improvement in bone mass and a decrease in bone turnover in response to estrogen treatment in another published report.

The proposed study is a prospective, double blind, randomized, placebo-controlled trial of the effect of alendronate on bone in perimenopausal women as a function of lead exposure. The subjects can be randomized to placebo or alendronate prior to determination of bone lead status.

Due to having the highest risk for development of osteoporosis and subsequent release of lead into the blood, we can enroll only perimenopausal (i.e., 50-60 years old) white/Hispanic female. Subjects can thus be matched for sex, race, and age. Subsequently, a KXRF-based bone lead level can be obtained. Using the median bone lead content of the study population in pg/g as the cutoff, subjects can be dichotomized into high versus low lead exposure groups, generating four groups:

| High Bone Lead Content | Low Bone Lead Content |
|---|---|
| White/Hispanic females-placebo | White/Hispanic females-placebo |
| White/Hispanic females-alendronate | White/Hispanic females-alendronate |

Subjects can have DEXA-based BMD measurements, calcaneal ultrasound BMD measurements, and KXRF-based bone lead levels at entry and at 12 and 24 months after randomization. In addition, bone metabolic parameters (calcium, phosphate, PTH, bone specific alkaline phosphatase, osteocalcin, vitamin D levels, collagen I urinary N-telopeptides) and blood lead level levels can be obtained at baseline. The blood lead levels, N-telopeptides, and other metabolic markers can be repeated 3 and 6 months after randomization, since we expect relatively short term responses of these parameters to the bisphosphonate treatment. We can also perform blood lead measurements at the 12 and 24 month time points.

We hypothesize that (1) Alendronate treatment can decrease bone resorption in lead-exposed perimenopausal women as measured by urinary N-telopeptide levels; (2) Alendronate treatment can result in lower blood lead levels and maintenance of higher bone lead levels in perimenopausal lead-exposed women; and (3) an increase in BMD can occur in alendronate-treated perimenopausal, lead-exposed women as is seen in women with otherwise normal osteoporotic bone.

Subjects can have DEXA-based BMD measurements, calcaneal ultrasound BMD measurements, and KXRF-based bone lead levels at entry and at 12 and 24 months after randomization. In addition, bone metabolic parameters (calcium, phosphate, PTH, bone specific alkaline phosphatase, osteocalcin, vitamin D levels, collagen I urinary N-telopeptides) and blood lead level levels can be obtained at baseline. The blood lead levels, N-telopeptides, and other metabolic markers can be repeated 3 and 6 months after randomization, since we expect relatively short term responses of these parameters to the bisphosphonate treatment. We can also perform blood lead measurements at the 12 and 24 month time points.

Subjects can be randomly assigned to either placebo or 70 mg of alendronate per week for two years. None of the project staff are involved in randomization. A pharmacist can conduct randomization prior to determination of lead exposure status using a random number table. Subjects can be divided into populations with high and low lead exposure by bone lead KXRF measurement subsequently. This approach assures minimum chance of bias in the randomization. The medications provided by Dr. Orloff can be numerically coded and the patients, clinical coordinator, project staff, and investigators can have no knowledge of the codes until this is provided after enrollment of all patients and completion of all data collection at the end of the trial, in order to maintain a strictly double blinded format for the study.

We can use the 70 mg once weekly dosage of alendronate. A study reports that patients receiving this regimen had increases in BMD comparable to patients who received alendronate 10 mg daily, but had fewer gastrointestinal symptoms. This regimen may improve compliance and reduce study attrition. The study can include only patients with osteopenia as defined by DEXA. Thus treatment with alendronate is potentially beneficial and not harmful, yet not clinically necessary, ensuring that placebo patients are not harmed in any way by the lack of treatment. All subjects can receive tablets of calcium carbonate containing 500 mg elemental calcium, and 200 I.U. of vitamin D and be instructed to consume two tablets daily to ensure minimum intake of 1000 mg calcium and 400 I.U. of vitamin per day.

Alendronate is a bisphosphonate and is standard therapy for osteoporosis. Contraindications are hypersensitivity, hypocalcemia, esophageal abnormalities, vitamin D deficiency, and renal insufficiency. Particularly in the 70 mg weekly dosing formulation, it has minimal side effects. The most common side effects (and incidence) are gastrointestinal and include abdominal pain (3.7%), esophageal ulcer (1.5%), diarrhea (3.1%), constipation (0.6%), flatulence (2.6%), dyspepsia (2.7%), abdominal distension (1.0%), and dysphagia (1.0%). The incidence of gastrointestinal side effects was not significantly different when compared to placebo. Case reports indicate that most patients with symptoms were not taking the dose with a full glass of water or not remaining in an upright position for 30 minutes after the dose. Other side effects (and incidence) include musculoskeletal pain (2.9%), rash (<0.1%), and headache (2.6%).

Ordinarily when patients are started on therapy, they are advised to report any adverse side effects to the treating physician (most commonly, gastrointestinal intolerance), but are not re-evaluated further for 1-2 years at which time follow-up densitometry is arranged. Therefore close monitoring is not ordinarily conducted in clinical practice. All patients can be informed on potential adverse effects of alendronate therapy with written instructional materials prior to randomization, and can be queried regarding adverse effects at each visit (3, 6, 12, 24 months after enrollment) and withdrawn from the study if adverse events are noted.

We determined the sample size required to discern a difference in BMD between the alendronate group and placebo group, stratified by cumulative lead exposure status (high vs. low). The main outcome in this study is a change in BMD. Although this is an intermediary outcome, it is highly associated with clinical outcomes. Two meta-analyses report that an increase in BMD is associated with a decreased risk of fractures. Most relevantly, BMD as an outcome measure, in comparison to fracture rates, enables us to conduct this study with fewer subjects.

We based the sample size on a two-tailed comparison of means. We initially determined the clinically relevant difference in BMD that can be expected among our subjects receiving alendronate. Several randomized trials of alendronate (5-10 mg per day for 2 years) among post-menopausal women found significant differences in mean vertebral BMD between treatment and placebo groups ranging from 5.2-8.7%. Some of these studies also assessed fracture rates, and found it to be significantly lower among treated subjects than those who received placebo. We therefore assumed that the clinically relevant difference in vertebral BMD due to alendronate to be 7.0%.

We obtained mean vertebral BMD from a sample of four white, female patients who had been screened for osteoporosis at our center with a Lunar Prodigy DEXA scanner. Their age ranged from 50.9-55.0 years, and all were healthy and without a history of chronic diseases or medications. From their BMD measurements we calculated a mean BMD of L1-L4 to be 1.099 gm/cm2; 7.0% of that value is 0.077 gm/cm2, corresponding well with the values in the database for normals incorporated into the software of the densitometer.

From the aforementioned analysis, we calculated the standard deviation of vertebral BMD to range from 0.1180.147 gm/cm2. To be conservative, we selected the highest value within that range—0.147 gm/cm2. This also is similar to the S.D. estimated from the normative database included in the densitometer software.

We selected a two-sided α-error to be 5%, and selected a power (1–β) of 80%. Based on these assumptions, we estimate that 58 subjects per treatment arm, or 116 subjects. Given we are stratifying by lead exposure status (high versus low), a total of 232 subjects are needed. Assuming a 20% attrition, a rate somewhat higher than reported in other trials after 2 years, 279 subjects need to be enrolled.

In a separate analysis which we performed, the number of patients derived above for bone density measurements was found to provide >90% power to detect a blood lead difference in the groups of 1 pg/dl, one of our other important outcome measures.

In one embodiment, BMD would be obtained only at the lumbar vertebrae, hip sites, calcaneus, and total body. Ultrasound measurements would be made at the calcaneus.

Blood lead levels can be measured by graphite furnace atomic absorption spectrometry at the Wadsworth Laboratory. The laboratory is certified under CLIA '88 and by OSHA, and has successfully participated in more than 7 national or international proficiency testing programs for the assay of blood lead levels. Full details are published at their web site: www.wadsworth.org/testing/lead/index.htm.

Blood samples are assayed twice on two days and the mean is reported. The typical within-run precision for a single instrument, defined as the standard deviation of 10 replicate measurements, ranges from 0.23-0.26 µg/dL for the range 1.0-20.0 µg/dL. Between-run precision, defined as the standard deviation of measurements made over 5 days, ranges from 0.1-0.4 µg/dL for the range 1.0-10.0 µg/dL. Accuracy, defined as the difference between the value found and the target value of certified reference standards is better than 1.0 µg/dL for standards below 15 µg/dL, or 10% for standards above 15 µg/dL. This method is the basis for one now adopted by the National Committee for Clinical Laboratory Standards.

We obtained mean vertebral BMD from a sample of four white, female patients who had been screened for osteoporosis at our center with a Lunar Prodigy DEXA scanner. Their age ranged from 50.9-55.0 years, and all were healthy and without a history of chronic diseases or medications. From their BMD measurements we calculated a mean BMD of L1-L4 to be 1.099 gm/cm$^2$; 7.0% of that value is 0.077 gm/cm$^2$, corresponding well with the values in the database for normals incorporated into the software of the densitometer.

From the aforementioned analysis, we calculated the standard deviation of vertebral BMD to range from 0.118-0.147 gm/cm$^2$. To be conservative, we selected the highest value within that range—0.147 gm/cm$^2$. This also is similar to the S.D. estimated from the normative database included in the densitometer software.

We selected a two-sided α-error to be 5%, and selected a power (1–β) of 80%. Based on these assumptions, we estimate that 58 subjects per treatment arm, or 116 subjects. Given we are stratifying by lead exposure status (high versus low), a total of 232 subjects are needed. Assuming a 20% attrition, a rate somewhat higher than reported in other trials after 2 years, 279 subjects need to be enrolled.

In a separate analysis which we performed, the number of patients derived above for bone density measurements was found to provide >90% power to detect a blood lead difference in the groups of 1 µg/dl, one of our other important outcome measures.

The DEXA-based measurement of BMD poses an extremely low risk to the subjects. The X-ray exposure from the DEXA scanner is minimized by using a small field that measures 19 mm by 3 mm. In addition, lead oxide shielding surrounds the X-ray tube inside the housing assembly; this reduces radiation levels to background levels outside of the radiation field. The total dose of radiation can vary for each site: vertebrae—9 EtGy, total body—0.4 ftGy. In comparison, the radiation dose from a chest X-ray is much higher: about 10,000 gGy. Thus, the radiation dose to a human subject undergoing a BMD measurement is extremely low, and there is no evidence that any adverse effect can occur at these dosages. Children have been extensively studied for measurement of BMD with this technique. This measurement is also well tolerated by children. Among 28 subjects in our pilot study, all tolerated the entire procedure well.

The ultrasound instrument to measure BMD of the calcaneus is very safe. There are no known contraindications associated with the use of this instrument; no adverse reactions or deaths were reported in 9957 examinations (Achilles Express Operating Manual, March 1999). There is a theoretical risk of transmission of bacteria onto the heel, and therefore subjects who have an open sore on one heel can have the sore covered with sterile 2×2 gauze dressing. This measurement is also well tolerated by children. Among 9 subjects in our pilot study, all tolerated the entire procedure well.

The KXRF instrument to measure bone lead levels is very safe. A single measurement of the tibia emits an effective dose of 35 nSv. This radiation dose is minimal and corresponds to 5-10 minutes of natural background radiation delivered to the whole body. This is about 0.1% the standard dose of a chest X-ray. Children and adolescents have been extensively studied for measurement of bone lead with this technique. Studies also report the procedure is well accepted with a 30-minute scan time.

Using principles of the present invention, one can conduct a randomized, placebo controlled trial of alendronate on osteopenic subjects. We feel placebo treatment is not unethical among such patients. Monitoring the BMD at this level of bone loss is an accepted clinical approach. By the same token, treatment with alendronate among osteopenic patients is also acceptable since it may reduce the risk of progression to osteoporosis, and thus may have a beneficial effect. Any women whose bone loss progresses to osteoporosis (i.e., T-score <−2.5) during study period can be removed from the study and referred for treatment of her osteoporosis.

Alendronate (Fosamax™) is a standard therapy for treatment of established osteoporosis, and is also approved for treatment of at risk groups to prevent osteoporosis. With 70 mg, once a week dosing regimens, side effects are minimal, but can include bone pain or gastrointestinal intolerance. Patients can be evaluated at each visit (3, 6, 12, and 24 months after enrollment) for side effects, and withdrawn from the study if drug intolerance occurs.

What is claimed is:

1. A method of correcting a bone density value for an effect of lead in the detection of osteopenia, the method comprising:
   determining an apparent bone density in a patient;
   applying a correction factor to the apparent bone density, the correction factor being based on a lead level;
   deriving a corrected bone density value of the patient; and
   reporting the corrected bone density value to an output.

2. The method of claim 1, wherein the apparent bone density comprises an apparent bone mineral density.

3. The method of claim 1, wherein the lead level comprises a blood lead concentration, and both the apparent bone density and the blood lead concentration are measured in the same patient.

4. The method of claim 1, wherein the lead level comprises a bone lead level, and both the apparent bone density and the bone lead level are measured in the same patient.

5. The method of claim 4, wherein the bone lead level is determined by x-ray fluorescence.

6. The method of claim 5, wherein the x-ray fluorescence comprises K shell x-ray fluorescence.

7. The method of claim 6, wherein x-rays are emitted from a $^{57}$Co source.

8. The method of claim 1, wherein the lead level comprises an average lead level in a population.

9. The method of claim 1, wherein the determining of an apparent bone density comprises making a dual-energy x-ray absorptiometry measurement of at least one bone in the patient.

10. The method of claim 9, wherein the at least one bone comprises a calcaneus.

11. The method of claim 1, wherein the correction factor is applied to the apparent bone density according to the equation:

$$\text{corrected bone density} = \text{apparent bone density} \times (A(\text{blood lead level}) + B)/B.$$

12. The method of claim 11, wherein A is about −1.

13. The method of claim 12, wherein A is about −1.08.

14. The method of claim 13, wherein A is about −1.075.

15. The method of claim 11, wherein B is about 170 to about 180.

16. The method of claim 15, wherein B is about 175.

17. The method of claim 16, wherein B is about 175.4.

18. The method of claim 1, wherein the output comprises a document.

19. The method of claim 1, wherein the output comprises a graphic display.

* * * * *

UNITED STATES PATENT AND TRADEMARK OFFICE
CERTIFICATE OF CORRECTION

PATENT NO. : 7,386,337 B2
APPLICATION NO. : 10/428367
DATED : June 10, 2008
INVENTOR(S) : J. Edward Puzas It is certified that error appears in the above-identified patent and that said Letters Patent is hereby corrected as shown below:

In claim 12, c column 22, line 18, "wherein A is about -I." should read --wherein A is about -1.--.

Signed and Sealed this

Twenty-eighth Day of October, 2008

JON W. DUDAS
*Director of the United States Patent and Trademark Office*